(12) United States Patent
Liman et al.

(10) Patent No.: US 7,205,430 B2
(45) Date of Patent: Apr. 17, 2007

(54) PRODUCTION OF DI- AND POLYISOCYANATES OF THE DIPHENYLMETHANE SERIES WITH DEFINED ACIDITY

(75) Inventors: Ulrich Liman, Langenfeld (DE); Heinz-Herbert Müller, Krefeld (DE); Robert Vieler, Dormagen (DE); Ralf Echterhoff, Dormagen (DE)

(73) Assignee: Bayer MaterialScience Aktiengesellschaft, Levekrusen (DE)

( * ) Notice: Subject to any disclaimer, the term of this patent is extended or adjusted under 35 U.S.C. 154(b) by 147 days.

(21) Appl. No.: 11/048,667

(22) Filed: Feb. 1, 2005

(65) Prior Publication Data

US 2005/0240054 A1 Oct. 27, 2005

(30) Foreign Application Priority Data

Feb. 4, 2004 (DE) ...................... 10 2004 005 320

(51) Int. Cl.
*C07C 263/00* (2006.01)
*C07C 249/00* (2006.01)
(52) U.S. Cl. ................ 560/347; 560/333; 560/352
(58) Field of Classification Search ............. 560/333, 560/347, 352
See application file for complete search history.

(56) References Cited

U.S. PATENT DOCUMENTS

| 3,155,699 A | 11/1964 | Powers ............... 260/453 |
| 4,414,074 A | 11/1983 | Ellendt et al. ............. 203/21 |
| 6,576,788 B1 | 6/2003 | Penzel et al. ............ 560/333 |
| 2004/0171869 A1 | 9/2004 | Reif et al. ............ 560/347 |

Primary Examiner—J. Parsa
(74) Attorney, Agent, or Firm—Joseph C. Gil; N. Denise Brown

(57) ABSTRACT

The invention relates to a process for the production of di- and polyisocyanates of the diphenylmethane series and mixtures thereof, in which aniline and formaldehyde are reacted in the presence of an acid catalyst to form di- and polyamines of the diphenylmethane series; the di- and polyamines of the diphenylmethane series are phosgenated, optionally in the presence of a solvent, to obtain a crude di- and polyisocyanate; from the crude di- and polyisocyanate, at least one fraction containing at least 5 wt. % 3-ring and multi-ring MDI and at least one fraction containing at least 95 wt. % 2-ring MDI are separated by distillation, and the acidities of the fraction containing at least 5 wt. % 3-ring MDI and multi-ring MDI, and/or the fraction containing at least 95 wt. % 2-ring MDI are determined analytically; and an acidic compound is added to the fraction containing at least 5 wt. % 3-ring MDI and multi-ring MDI, and/or the fraction containing at least 95 wt. % 2-ring MDI, so that the desired acidity is achieved.

10 Claims, No Drawings

PRODUCTION OF DI- AND POLYISOCYANATES OF THE DIPHENYLMETHANE SERIES WITH DEFINED ACIDITY

BACKGROUND OF THE INVENTION

The present invention relates to a process for the production of di- and polyisocyanates of the diphenylmethane series and mixtures thereof, and to a process for the production of polyurethanes from the di- and polyisocyanates of the diphenylmethane series.

Aromatic isocyanates are very important raw materials for the production of polyurethane materials. In terms of quantity, the di- and polyisocyanates of the diphenylmethane series (MDI) play the leading role in this.

The term polyisocyanates of the diphenylmethane series means isocyanates and mixtures of isocyanates which correspond to the following structure:

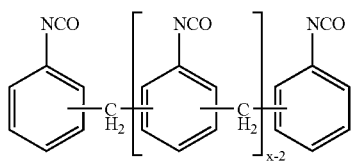

x = 2 to n where n denotes a natural number>2.

Similarly, the term polyamines of the diphenylmethane series means compounds and mixtures of compounds which correspond to the following structure:

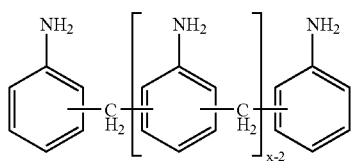

x = 2 to n where n denotes a natural number>2.

It is known that di- and polyisocyanates of the diphenylmethane series (MDI) are produced by phosgenation of the corresponding diamines and polyamines of the diphenylmethane series (MDA). The diamines and polyamines of the diphenylmethane series (MDA) are themselves produced by condensation of aniline and formaldehyde. By phosgenation of the diamines of the diphenylmethane series, the corresponding diisocyanates 2,2'-MDI, 2,4'-MDI and 4,4'-MDI are obtained, which are described in specialist circles as 2-ring (i.e. bi-nuclear) compounds of MDI (i.e. diisocyanates of the diphenylmethane series). During the condensation of aniline and formaldehyde, however, the 2-ring MDA (i.e. methylenediphenyldiamine) continues to react further with formaldehyde and aniline to form multi-ring MDA types, which, after phosgenation, represent the multi-ring (i.e. polynuclear) content in the polymeric MDI (polyisocyanates of the diphenylmethane series).

For many practical product applications, it is preferred that a defined acid content be established in the MDI. This standardization compensates for any variations in reactivity caused by secondary compounds in the reaction chain from aniline to MDI. These secondary compounds have an influence on the acid content of the MDI during processing with compounds which contain isocyanate-reactive hydrogen atoms, such as, for example, the polyols used in polyurethane chemistry.

In practice, the acid content in MDI is expressed as acidity in polymeric MDI (PMDI) and/or monomeric MDI (MMDI), or as hydrolysable chlorine in MMDI. This acidity value is determined, in practice, by reacting MDI with lower alcohols such as, e.g. methanol (cf. e.g. ASTM D5523-94 for monomeric MDI or ASTM5629-99 or 6099-03 for polymeric MDI).

The acid content in MDI is determined, as described in the current state of the art, by the processing parameters in the production process for the MDA bases by the formation of secondary components in the MDA, which is dependent on the relevant MDA process parameters, and during the phosgenation of MDA to MDI, and subsequent work-up. Because of the multi-step reaction chain and the variations and changes in the throughput and process parameters during production, this leads in practice to unavoidable variations in the acid content. Values for the acid content in the MDI as MDI acidity of up to 500 ppm acid (calculated as HCl) are generally achieved. However, deviations from the desired acidity sometimes occur. These variations in acidity within the product quality of a manufactured MDI result in undesirable deviations in the reaction behavior of the MDI during the subsequent polyurethane production.

In general, it is correct that as the acid content increases, the reactivity of MDI (i.e. the relative reactivity of isocyanate to polyol) slows down or decreases. However, since during polyurethane processing the reactivity should generally be defined by the catalysis in the polyol, it is essential for safe and reproducible processing for the MDI component to have constant, and consistent, reactivity. The acid content achieved during production as described in the prior art, and particularly in the case of MMDI (monomeric MDI), can even be so low such that undesirable secondary reactions occur during polyurethane processing (e.g. alkali-catalysed polyisocyanurate reaction).

In the marketplace, therefore, the various MDI products commercially available are provided with a specification value for the acidity or the hydrolysable chlorine content (i.e. HC value). The analyses of the acidity are generally performed according to the ASTM test methods mentioned above, which describe the content of acid released during reaction with compounds which contain active hydrogen atoms. This value is generally calculated as HCl.

SUMMARY OF THE INVENTION

The object of the present invention is therefore to provide a simple process for the production of di- and polyisocyanates of the diphenylmethane series and mixtures thereof, with a defined and constant value for the acid content (i.e. acidity, hydrolysable chlorine content). This process should provide a constant MDI product in which the quality, as based on acid content, can be reliably guaranteed.

The invention relates to a process for the production of di- and polyisocyanates of the diphenylmethane series and mixtures thereof. This process comprises a) reacting aniline and formaldehyde in the presence of an acid catalyst to form di- and polyamines of the diphenylmethane series, b) phosgenating the di- and polyamines of the diphenylmethane series, optionally in the presence of a solvent, to obtain a crude di- and polyisocyanate, c) separating at least one fraction containing at least 5 wt. % of 3-ring and multi-ring MDI and at least one fraction containing at least 95 wt. % of 2-ring MDI, from the crude di- and polyisocyanate, by distillation, d) determining analytically the acidities of the fraction containing at least 5 wt. % of 3-ring and multi-ring MDI, and/or of the fraction containing at least 95 wt. % of 2-ring MDI, and e) adding an acidic compound to the fraction containing at least 5 wt. % of 3-ring and multi-ring MDI and/or to the fraction containing at least 95 wt. % of 2-ring MDI, such that the desired acidity of each fraction is achieved.

The fractions produced in step e) are then preferably poured into containers. These fractions are then available as an isocyanate component with precisely adjusted acidity, and are suitable for the production of modified isocyanates, as products for blending with other isocyanate fractions, and for the production of prepolymers and/or polyurethanes.

By the addition of the acidic, organic or inorganic compounds to the MDI as an additive in step e), the specified values for acid content (i.e. acidity, hydrolysable chlorine content) of the MDI can be achieved accurately and reproducibly. This is true, regardless of the production process used to make the MDI. Thus, the present invention relates to a process for the production of MDI and mixtures thereof, in which the acidity and the hydrolysable chlorine value of the MDI or mixtures thereof are adjusted in a targeted manner by adding acidic, particularly halogen-containing and especially chlorine-containing compounds, after separating the crude MDI mixture by distillation into the isomers or mixtures of isomers. As a result of the targeted adjustment of the acidity and of the hydrolysable chlorine value, a constant reactivity of the MDI is guaranteed here. This MDI also satisfies the previously existing product specifications.

The polyamine or mixture of polyamines of the diphenylmethane series which is used obtained in step a) of the process according to the invention, by the condensation of aniline and formaldehyde, in the presence of an acid catalyst are described by H. J. Twitchett, Chem. Soc. Rev. 3(2), 209 (1974); and W. M. Moore in: Kirk-Othmer Encycl. Chem. Technol., $3^{rd}$ ed., New York, 2, 338–348 (1978)). It is immaterial to the present process whether aniline and formaldehyde are first mixed in the absence of the acid catalyst, and the acid catalyst is then added, or whether a mixture of aniline and acid catalyst is reacted with formaldehyde. Suitable mixtures of polyamines of the diphenylmethane series are conventionally obtained by condensation of aniline and formaldehyde in a molar ratio of aniline to formaldehyde of 20:1 to 1.6:1, preferably 10:1 to 1.8:1, and a molar ratio of aniline to acid catalyst of 20:1 to 1:1, preferably 10:1 to 2:1.

Formaldehyde is normally used as an aqueous solution on an industrial scale. Thus, the water content can vary from 1 to 95% by wt., based on the total weight of the solution. An aqueous solution containing from 50 to 80% by wt. of water (based on the total weight of the solution) is preferably used. However, other compounds which provide methylene groups, such as, e.g. polyoxymethylene glycol, para-formaldehyde or trioxane, can also be used.

Strong organic, and preferably inorganic acids, have proved suitable as the acid catalysts. Suitable acids are, e.g. hydrochloric acid, sulfuric acid, phosphoric acid and methanesulfonic acid. Hydrochloric acid is preferably used.

In a preferred embodiment of the process, aniline and the acid catalyst are first mixed together. This mixture is mixed with formaldehyde in a suitable manner in another step, optionally after the dissipation of heat, at temperatures of between about 20° C. and about 100° C., preferably between about 30° C. and about 70° C., and then subjected to a preliminary reaction in suitable residence time apparatus. The preliminary reaction takes place at temperatures of between about 20° C. and about 100° C., and preferably in the temperature range of from about 30° C. to about 80° C. Following the mixing and preliminary reaction, the temperature of the reaction mixture is brought, either stepwise or continuously, and optionally under excess pressure, to a temperature of from about 100° C. to about 250° C., preferably to a temperature of from about 100° C. to about 180° C., and more preferably to a temperature of from about 100° C. to about 160° C.

In another embodiment of the process, however, it is also possible first to mix together and react aniline and formaldehyde, in the absence of the acid catalyst, in the temperature range of from about 5° C. to about 130° C., preferably from about 40° C. to about 100° C., and more preferably from about 60° C. to about 90° C. In this embodiment, condensation products of aniline and formaldehyde (i.e. so-called aminals) are formed. Following the aminal formation, water present in the reaction mixture can be removed by phase separation or other appropriate process steps such as, e.g., by distillation. The condensation product is then mixed with the acid catalyst in a suitable manner in another process step, and subjected to a preliminary reaction in a residence time apparatus at a temperature of about 20° C. to about 100° C., preferably about 30° C. to about 80° C. The temperature of the reaction mixture is then brought, either stepwise or continuously, and optionally under excess pressure, to a temperature of from about 100° C. to about 250° C., preferably to a temperature of from about 100° C. to about 180° C., and more preferably to a temperature of from about 100° C. to about 160° C.

In order to work up the acidic reaction mixture, the reaction mixture is neutralised with a base, as is described in the prior art. According to the prior art, the neutralisation conventionally takes place at temperatures of, for example, from about 90 to about 100° C. (see H. J. Twitchett, Chem. Soc. Rev. 3(2), 223 (1974)). Suitable compounds to be used as bases are, for example, the hydroxides of the alkali and alkaline earth elements. Aqueous NaOH is preferably used.

After the neutralisation, the organic phase is separated from the aqueous phase by suitable processes as is disclosed in the prior art. One such suitable process is, for example, by phase separation in a separating flask. This separation of organic and aqueous phases can take place at the same temperature at which the neutralisation of the acidic rearrangement mixture took place. The product-containing organic phase which remains after separating off the aqueous phase is subjected to washing (as described in the prior art) to separate off salts and excess base. The purified organic phase is then freed of excess aniline and other substances present in the mixture (e.g. other solvents) by suitable physical separation processes and methods, such as, e.g., distillation, extraction or crystallisation.

The polyamine of the diphenylmethane series (crude MDA) thus obtained from step a) is reacted in step b) with phosgene, optionally in the presence of an inert organic solvent, by the known methods to form the corresponding isocyanates.

The molar ratio of crude MDA to phosgene is usefully set such that there are 1 to 10 moles, preferably 1.3 to 4 moles, of phosgene per mole $NH_2$ group present in the reaction mixture. Suitable inert solvents include, for example, chlorinated, aromatic hydrocarbons such as, e.g., monochlorobenzene, dichlorobenzenes, trichlorobenzenes, the corresponding toluenes and xylenes, as well as chloroethylbenzene. Monochlorobenzene, dichlorobenzene or mixtures of these chlorobenzenes are preferably used as inert organic solvents. The quantity of solvent is preferably set (or adjusted) such that the reaction mixture has an isocyanate content of 2 to 40 wt. %, preferably between 5 and 20 wt. %, based on the total weight of the reaction mixture. The reaction of crude MDA with phosgene is carried out at temperatures of from about 50 to about 250° C. and under pressures from atmospheric pressure up to 50 bar. It is preferable to work at temperatures of from about 70 to about 180° C., and pressures of from 2 to 20 bar.

After completion of the phosgenation, the excess phosgene, the inert organic solvent, the HCl formed and/or mixtures thereof are separated from the reaction mixture by suitable processes (e.g. by distillation). For this, the pressure is reduced stepwise to a vacuum and the remaining phosgene excess and the HCl formed are evaporated and separated off. The solvent is then reduced stepwise, preferably by evaporation, with further reduction of the absolute pressure to down to 1 mbar, preferably down to 5 mbar. At the same time, i.e. parallel to this, the temperature is increased or raised until the solvent is almost completely removed, i.e down to a concentration of far less than 0.1%. Finally, in step b), a crude di- and polyisocyanate (crude MDI mixture) is obtained.

The separation can take place by distillation under vacuum or by crystallisation. A combination of the two processes is also possible.

In step c), at least one fraction which contains at least 5 wt. % of 3-ring and multi-ring MDI (i.e. higher ring compounds of MDI or PMDI), and at least one fraction which contains at least 95 wt. % of 2-ring MDI (i.e. monomeric MDI) are separated by distillation from the crude di- and polyisocyanate.

The fraction containing at least 5 wt. % of 3-ring and multi-ring MDI preferably has an acidity of from 5 to 500 ppm (calculated as HCl). The fraction containing at least 95 wt. % of 2-ring MDI preferably has an acidity of from 0.1 to 50 ppm (calculated as HCl). The values given for the acidity here are based on the method of determining acidity as described in Example 1 below.

In step d), the acidities of the fraction that contains at least 5 wt. % of 3-ring and multi-ring MDI and/or of the fraction that contains at least 95 wt. % of 2-ring MDI, and which are produced in step c) are determined analytically. This can take place in accordance with the specifications according to ASTM D5523-94 for monomeric MDI, or ASTM5629-99 or 6099-03 for polymeric MDI, or by the method described in Example 1 for monomeric MDI or polymeric MDI. For monomeric MDI, however, the determination of acidity generally takes place as a determination of the hydrolysable chlorine value. This determination can take place by the method described in Example 2.

Acidity variations in the range of up to 50% can typically occur in PMDI with an average acidity of, for example approx. 100 ppm. These variations occur as a result of variations or changes in the throughput and process parameters during production and/or in different production plants. An acidity variation of less than 5% is, however, desirable. This is achieved in that, depending on the existing or actual acidity, the acidity-active additive is added to the MDI in a quantity such that the final acidity lies above the maximum value of actual acidity due to the process-related variation range of the MDI in question. Thus, in this example, the maximum value would be 100 ppm+50 ppm=150 ppm. The devices which are commercially available for metering the acid compound into the isocyanate are so accurate that the range of variation achieved is negligible. The case of MMDI is similar, with an approximate acidity of e.g. 10 ppm with variations of up to 100%. In this case, the acid compound is similarly added to the MMDI as an acidity-active additive.

In step e), an acid compound is added to the fraction containing at least 5 wt. % of 3-ring and multi-ring MDI, and/or to the fraction containing at least 95 wt. % of 2-ring MDI, both of which fractions were obtained in step c), so as to achieve the desired acidity for one or both of the fractions.

Gaseous HCl can be used for this purpose. Since the handling of HCl as a gas involves complex apparatus for metering, it is preferred to use liquid or solid organic compounds that increase the acidity value. Such compounds include, for example, benzotrichloride, benzoyl chloride, phthaloyl dichloride, terephthaloyl dichloride, isophthaloyl dichlorides, p-toluenesulfonyl chloride, or other organic acid chlorides. Organic acids that increase the acidity value are also suitable. Some examples of such organic acids include compounds such as, e.g., chloropropanoic acid. Preferred organic compounds include those that are readily soluble in MDI and which, at the same time, have a low vapor pressure and do not modify the other properties of the desired isocyanate addition products in the finished article.

Anhydrous mineral acids such as, e.g. HCl gas or other hydrogen halides, phosphoric acid or other phosphorus-containing anhydrous acids, sulfuric acid and other mineral acids are suitable as inorganic acid compounds to be added in step e) of the present invention. Also suitable to be added as the acidic compound in step e) are inorganic anhydrous Lewis acids, such as e.g. aluminium trichloride, boron trifluoride, boron trichloride, etc.

Suitable organic acid compounds which can be used as the acidic compound and that increase the acidity value include aliphatic or cycloaliphatic carboxylic acid halides such as, e.g., acetyl chloride, trichloroacetyl chloride or N-chloroacetamide or N-bromosuccinimide; aromatic carboxylic acid halides such as, e.g., benzoyl chloride, phthaloyl chloride, terephthaloyl dichloride, isophthaloyl dichloride; aromatic, aliphatic or cycloaliphatic carbamyl chlorides such as, e.g., N-phenylcarbamyl chloride, tert.-butylcarbamyl chloride; acidic chlorosilane compounds such as, e.g., trimethylsilyl chloride, trimethylsilyl trifluoromethanesulfonate; sulfonic acid halides such as, e.g., tosyl chloride; or other carboxylic acid derivatives such as, e.g., anhydrides, or mixtures thereof. Benzoyl chloride, phthaloyl dichloride, terephthaloyl dichloride, butylcarbamoyl chlorides, trimethylsilyl trifluoromethanesulfonate are preferably used as organic acid compounds.

Aromatic or aliphatic acid chlorides or carbamyl chlorides are preferably used to adjust the acidity for MDI, and for the MDI mixtures with 2-ring MDI contents of more than 80 wt. %, and the derivatives and modifications thereof, such as allophanates, carbodiimides, uretonimines, uretdiones and prepolymeric urethanes and/or prepolymeric ureas. Aromatic or aliphatic acid chlorides or carbamyl chlorides which have no negative effect on the production of the polyurethanes and which have a low vapor pressure are preferably used here. Benzoyl chloride, terephthaloyl dichloride, isophthaloyl dichloride, phenylcarbamyl chloride, tert.-butylcarbamyl chloride are more preferably used.

The introduction of the acid compound can take place directly into the desired MDI or in the form of a more highly concentrated stock solution, which is preferably prepared with the corresponding MDI and which does not alter the specification of the desired MDI.

As a result of the process according to the invention, a defined acidity or a defined hydrolysable chlorine content, is achieved in the MDI obtained. This defined acidity or defined hydrolysable chlorine content provides a constant and defined reaction behavior of MDI towards compounds which contain active hydrogen atoms. This, in turn, has a positive effect on problem-free processing in the production of finished polyaddition products produced from the MDI.

In another embodiment of the process of the present invention, in addition to the acidic inorganic or organic compounds or mixtures thereof, inert transition metal compounds, and preferably transition metals from subgroup VIII, more preferably iron compounds in the form of inorganic or organic iron salts or iron complexes, can also be added in step e). These inert transition metal compounds accelerate the reaction of the isocyanate groups with the H-acid compound (polyol compound) during the subsequent polyurethane production. The PMDI and the MMDI may contain small trace amounts of iron resulting from the production process. These trace amounts of iron may be caused by corrosion and/or erosion of parts of the apparatus, which can vary markedly, and then lead to fluctuating reactivities. The variabilities in reactivity can be compensated by establishing a constant iron trace content by adding appropriate trace amounts of suitable iron compounds.

Suitable iron compounds for establishing a constant iron trace content include inorganic or organic iron salts of mineral acids, of aliphatic, alicyclic and aromatic carboxylic acids and alkoxides or iron complexes. The iron compounds added must be anhydrous. Suitable iron salts include, e.g., Fe(III) chloride, Fe(II) acetate, Fe(III) bromide, Fe(II) fluoride, Fe(II) iodide, Fe(II) fumarate, Fe(III) tribenzoate, Fe(III) trisalicylate, Fe(III) trilaurate, Fe(III) tripalmitate, Fe(III) tristearate, Fe(III) trioleate, Fe naphthenates, Fe(II) 2-ethylhexanoate, Fe(II) tris(4-cyclohexyl butyrate), Fe(III) ethoxide, Fe(III) i-propoxide. Suitable iron complexes include, e.g., Fe(III) acetylacetonate, Fe(III) benzoylacetonate, Fe(II) phthalocyanine, ferrocene, Fe(III) trifluoroacetylacetonate. It is preferred that Fe(III) chloride and/or Fe(III) acetylacetonate are used.

In addition, metal catalysts known in polyurethane processing such as, e.g., zinc chloride, dibutyltin dilaurate (DBTDL), tin octoate or other organic tin compounds, can also be added to enable the reactivity to be adjusted in a defined manner for specific applications. In this case, the addition takes place to the extent that the specified shelf life of generally 6 months can still be guaranteed.

The MDI products produced by the process according to the invention with a defined value for acidity can also be blended with one or more mixtures containing aromatic isocyanates. For the blending, in addition to the preferably used mixtures which contain di- and/or polyisocyanates of the diphenylmethane series already mentioned, mixtures containing toluene diisocyanate (e.g. 2,4-TDI, 2,6-TDI) or mixtures containing naphthalene diisocyanate (e.g. 1,5-NDI) or mixtures of these isocyanates can also preferably be used. In principle, however, other any other known aromatic and/or aliphatic mono-, di-, tri- or polyfunctional isocyanates can also be used for the blending.

The MDI products produced by the process according to the invention with a defined value for acidity can be employed for the conventional modification reactions of isocyanates, such as, e.g., for carbodiimidisation by temperature increase or addition of phospholene oxides and for the production of uretonimines based on the carbodiimides, or for the production of prepolymers from OH—functional polyesters, $C_2/C_3/C_4$ polyethers, uretdiones, allophanates, biurets or urea derivatives.

The fractions of diisocyanates of the diphenylmethane series produced according to the present invention are used as, among other things, blend components for other di- and polyisocyanates from the MDI series, and/or other isocyanates for the production of isocyanate components for use in the production of polyurethanes. The finished articles to be produced from these blended products cover the entire field of polyurethane chemistry. The following are mentioned here as examples: rigid foams for the insulation and refrigeration equipment industry, packaging foam, flexible foam and flexible moulded foam for furniture and the automotive industry, applications in the spectrum of the CASE, applications (coatings, adhesives, sealants, elastomers), semi-rigid PU foams, etc.

All ranges used throughout the present application are inclusive of upper and lower limits, unless otherwise stated. All ranges provided may also use any combination of upper and lower limits, inclusive, unless otherwise stated.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

Example 1

(Adjustment of the Acidity of a Polymeric MDI (PMDI)):

11 batches of a polymeric MDI were produced by steps a) through c) of the process described above in accordance with the present invention. The 11 batches had a content of 3-ring MDI and multi-ring MDI of 46 to 49 wt. %.

In step d), the acidity of the individual batches was determined analytically. This determination of the acidity occurred by the following method:

About 6 g of the MDI polymer sample were weighed to an accuracy of at least 0.01 g into a 250 ml beaker. 60 ml of chlorobenzene were then added and the MDI sample was dissolved in the added quantity of chlorobenzene. Then, 100 ml of methanol were added to the solution, the beaker was covered and the mixture was stirred for 30 min at ambient temperature using a magnetic stirrer. Finally, the mixture was titrated acidimetrically, using a methanolic potassium hydroxide standard solution with a molar concentration of approx. 0.01 mol/l, with a potentiometric end-point display.

The analysis showed that the individual batches had an acidity of 41.6+/−6.2 mg $H^+$/kg in the starting state, with a relative standard deviation of 14.9%.

In step e), the 11 batches of the polymeric MDI were then adjusted to an acidity of 100 mg/kg (calculated as $H^+$, standardised value) using hydrogen chloride gas. For this purpose, the quantity of hydrogen chloride gas needed for each individual batch to adjust the acidity to 100 mg $H^+$/kg was metered in. After the adjustment, the variability of the acidity values was clearly lower (100+/−3.5 mg $H^+$/kg, relative standard deviation 3.5%).

Example 2

(Adjustment of the Hydrolysable Chlorine Content for Monomeric MDI):

For monomeric MDI, the acidity of the MDI was determined as the hydrolysable chlorine value.

85 batches of a monomeric MDI were produced by steps a) through c) of the process described above in accordance with the present invention. The 85 batches had a 2-ring MDI content of >98.2 wt. %. The individual 2-ring MDI isomers were contained therein in the following quantities: 4,4'-MDI ($\geq$98.0%), 2,4'-MDI ($\leq$2.0%) and 2,2'-MDI ($\leq$0.3%), based on the sum (i.e. total weight) of the 2-ring MDI isomers.

In step d), the hydrolysable chlorine value was determined. This determination of the hydrolysable chlorine value occurred by the following method:

About 10 g of the MDI monomer sample were weighed into a 500 ml Erlenmeyer flask. The MDI monomer was then melted in a boiling water bath and dissolved in 40 ml of chlorobenzene. Then, 100 ml of propanol-(2) were added, the Erlenmeyer flask was covered and the reaction mixture was stirred for 5 min at ambient temperature using a magnetic stirrer. 100 ml of methanol were then added and the mixture was stirred for a further 5 min at ambient temperature. Next, 100 ml of water were then added, a reflux condenser was attached and the reaction mixture was heated to boiling point, while being stirred gently for 30 min. After cooling, 50 ml of acetone were added through the reflux condenser. Finally, the titration, using a silver nitrate standard solution with a molar concentration of approx. 0.002 mol/l, with a potentiometric end-point display.

The analysis showed that the individual batches have a hydrolysable chlorine content that varies markedly for the individual batches. The hydrolysable chlorine content is 27.4+/−5.3 mg HCl/kg for the 85 batches, with a relative standard deviation of 19.3%.

In step e), the 85 batches of monomeric MDI were then adjusted to a hydrolysable chlorine content of 100 mg/kg (calculated as HCl, standardised values) by adding isophthaloyl dichloride. For this purpose, the quantity of isophthaloyl dichloride needed for each individual batch to adjust the hydrolysable chlorine value to 100 mg HCl/kg was metered in. The isophthaloyl dichloride was added as a masterbatch, dissolved in a mixture of 45% by wt. of 4,4'-MDI and 55% by wt. of 2,4'-MDI. After the adjustment, the variability of the hydrolysable chlorine contents was clearly lower (100+/−3.3 mg HCl/kg; relative standard deviation 3.3%).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of di- and polyisocyanates of the diphenylmethane series and mixtures thereof, comprising
    a) reacting aniline and formaldehyde in the presence of an acid catalyst to form di- and polyamines of the diphenylmethane series,
    b) phosgenating the di- and polyamines of the diphenylmethane series from a), optionally in the presence of a solvent, to obtain a crude di- and polyisocyanate,
    c) separating at least one fraction containing at least 5 wt. % of 3-ring MDI and multi-ring MDI, and at least one fraction containing at least 95 wt. % 2-ring MDI, from the crude di- and polyisocyanate, by distillation,
    d) determining the acidities of the fraction containing at least 5 wt. % 3-ring MDI and multi-ring MDI, and/or the fraction containing at least 95 wt. % 2-ring MDI, and
    e) adding an acidic compound to the fraction containing at least 5 wt. % 3-ring MDI and multi-ring MDI, and/or to the fraction containing at least 95 wt. % 2-ring MDI, such that the desired acidity of each fraction is achieved.

2. The process of claim 1, wherein the acidic compound added in e) is selected from the group consisting of aliphatic carboxylic acid halides, aromatic carboxylic acid halides, cycloaliphatic carboxylic acid halides and mixtures thereof.

3. The process of claim 1, wherein the acidic compound added in e) is selected from the group consisting of aliphatic carbamic acid halides, aromatic carbamic acid halides, cycloaliphatic carbamic acid halides and mixtures thereof.

4. The process of claim 1, wherein the acidic compound added in e) comprises one or more acidic chlorosilane compounds.

5. The process of claim 1, wherein the acidic compound added in e) comprises one or more sulfonic acid halides.

6. The process of claim 1, wherein the acidic compound added in e) comprises one or more carboxylic acid anhydrides.

7. The process of claim 1, wherein in step e) an inert transition metal compound is added to one or both fractions in addition to the acidic compound.

8. The process of claim 7, wherein the inert transition metal compound contains a metal from subgroup VIII of the periodic table.

9. The process of claim 8, wherein the metal from subgroup VIII of the periodic table is iron.

10. The process of claim 7, wherein the inert transition metal compound is selected from the group consisting of iron acetylacetonate, a halide of a metal from subgroup VIII of the periodic table and zinc chloride.

* * * * *